(12) United States Patent
Fujimoto et al.

(10) Patent No.: US 11,871,897 B2
(45) Date of Patent: Jan. 16, 2024

(54) INFORMATION PROCESSING DEVICE, INFORMATION PROCESSING METHOD, AND INFORMATION PROCESSING PROGRAM

(71) Applicant: FUJIFILM CORPORATION, Tokyo (JP)

(72) Inventors: Yoshie Fujimoto, Kanagawa (JP); Shinichiro Konno, Kanagawa (JP); Shunsuke Kodaira, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 297 days.

(21) Appl. No.: 17/485,531

(22) Filed: Sep. 27, 2021

(65) Prior Publication Data

US 2022/0096026 A1   Mar. 31, 2022

(30) Foreign Application Priority Data

Sep. 30, 2020  (JP) ................. 2020-166467

(51) Int. Cl.
*A61B 8/14*   (2006.01)
*A61B 6/08*   (2006.01)
(Continued)

(52) U.S. Cl.
CPC .............. *A61B 6/08* (2013.01); *A61B 6/0414* (2013.01); *A61B 6/502* (2013.01); *A61B 6/54* (2013.01)

(58) Field of Classification Search
CPC ....... A61B 6/0414; A61B 6/461; A61B 6/025; A61B 6/5294; A61B 8/0825; A61B 8/463;
(Continued)

(56) References Cited

U.S. PATENT DOCUMENTS

2008/0087830 A1   4/2008  Kashiwagi
2009/0088637 A1*  4/2009  Mikami ............... A61B 8/5238
                                                     600/443
(Continued)

FOREIGN PATENT DOCUMENTS

JP    2004-321782 A    11/2004
JP    2007-236805 A     9/2007
(Continued)

OTHER PUBLICATIONS

English language translation of the following: Office action dated May 9, 2023 from the JPO in a Japanese patent application No. 2020-166467 corresponding to the instant patent application. This office action translation is submitted now in order to supplement the understanding of the cited references which are being disclosed in the instant Information Disclosure Statement.

*Primary Examiner* — Don K Wong
(74) *Attorney, Agent, or Firm* — SOLARIS Intellectual Property Group, PLLC

(57) ABSTRACT

An information processing device including at least one processor, wherein the processor is configured to: acquire a radiographic image captured by irradiating a breast compressed by a compression member with radiation; generate a projection image, which includes guide information serving as a guide in a case in which the breast is compressed and is capable of identifying whether the guide information is related to a right breast or a left breast, on the basis of a shape of the breast in the compressed state indicated by the radiographic image; and control an image projection unit which projects the projection image onto a first projection surface of the compression member such that the projection image is projected onto the first projection surface.

6 Claims, 13 Drawing Sheets

(51) Int. Cl.
*A61B 6/00* (2006.01)
*A61B 6/04* (2006.01)

(58) Field of Classification Search
CPC ....... A61B 5/708; A61B 6/4417; A61B 90/11;
A61B 5/0091; A61B 8/403; A61B
5/4312; A61B 6/463; G06T 2207/30068
See application file for complete search history.

(56) References Cited

U.S. PATENT DOCUMENTS

| | | |
|---|---|---|
| 2010/0054402 A1 | 3/2010 | Fischer et al. |
| 2017/0172531 A1 | 6/2017 | Sugiyama et al. |
| 2017/0367671 A1 | 12/2017 | Arai et al. |

FOREIGN PATENT DOCUMENTS

| | | |
|---|---|---|
| JP | 2008-086389 A | 4/2008 |
| JP | 2009-291336 A | 12/2009 |
| JP | 2010-253263 A | 11/2010 |
| JP | 2011-104149 A | 6/2011 |
| JP | 2014-195616 A | 10/2014 |
| JP | 2017-113540 A | 6/2017 |
| JP | 2017-225634 A | 12/2017 |

\* cited by examiner

| IDENTIFICATION INFORMATION | PROJECTION SURFACE SIZE INFORMATION | IRRADIATION FIELD |
|---|---|---|
| B001 | 24 × 30 | 24 × 30 |
| B002 | 18 × 24 | 18 × 24 |
| B003 | 10 × 24 | 18 × 24 |
| B004 | 10 × 10 | 9 × 9 |
| ⋮ | ⋮ | ⋮ |

INFORMATION PROCESSING DEVICE, INFORMATION PROCESSING METHOD, AND INFORMATION PROCESSING PROGRAM

CROSS-REFERENCE TO RELATED APPLICATIONS

The present application claims priority under 35 U.S.C. § 119 to Japanese Patent Application No. 2020-166467, filed on Sep. 30, 2020. The above application is hereby expressly incorporated by reference, in its entirety, into the present application.

BACKGROUND

Technical Field

The present disclosure relates to an information processing device, an information processing method, and an information processing program.

Related Art

In the related art, a radiography apparatus is known which performs radiography for the purpose of medical diagnosis. An example of this type of radiography apparatus is a mammography apparatus that captures an image of a breast of a subject. The mammography apparatus irradiates the breast of the subject which is an imaging part with radiation to capture an image in a state in which the breast is compressed by a compression plate.

In addition, a technique is known which projects guide information corresponding to the outward shape of the breast onto an imaging table in a mammography apparatus (see, for example, JP2017-113540A). JP2017-113540A describes a technique in which a projector projects, onto an imaging table, guide light including the position of the nipple of the breast, an image start position, and an image end position on the basis of the radiographic image of the breast captured in the past.

In the actual scene of mammography, the images of two left and right breasts of the same subject are generally captured. The user who performs imaging checks an imaging order in which the breast whose image is to be captured, an imaging item for the breast (for example, CC imaging, MLO imaging, enlargement imaging, and spot imaging), and the sequence of imaging are predetermined and then performs imaging in the sequence according to the imaging order using the mammography apparatus. In recent years, a technique has been required which can check whether to capture the image of the right breast or the image of the left breast while handling a mammography apparatus in order to improve the efficiency of an imaging operation.

SUMMARY

The present disclosure has been made in view of the above-mentioned problems, and an object of the present disclosure is to provide an information processing device, an information processing method, and an information processing program that can improve the efficiency of an imaging operation in mammography.

According to a first aspect of the present disclosure, there is provided an information processing device including at least one processor. The processor acquires a radiographic image captured by irradiating a breast compressed by a compression member with radiation, generates a projection image, which includes guide information serving as a guide in a case in which the breast is compressed and is capable of identifying whether the guide information is related to a right breast or a left breast, on the basis of a shape of the breast in the compressed state indicated by the radiographic image, and controls an image projection unit which projects the projection image onto a first projection surface of the compression member such that the projection image is projected onto the first projection surface.

According to a second aspect of the present disclosure, in the first aspect, the processor may generate the projection image while changing a display aspect depending on whether the guide information is related to the right breast or the left breast and control the image projection unit such that the projection image is projected onto the first projection surface.

According to a third aspect of the present disclosure, in the first or second aspect, the processor may generate the projection image including the guide information and left-right information indicating whether the guide information is related to the right breast or the left breast and control the image projection unit such that the projection image is projected onto the first projection surface.

According to a fourth aspect of the present disclosure, in the first or second aspect, the image projection unit may project an image onto a second projection surface different from the first projection surface of the compression member in addition to the first projection surface, and the processor may generate the projection image including the guide information and left-right information indicating whether the guide information is related to the right breast or the left breast and control the image projection unit such that the guide information is projected onto the first projection surface and the left-right information is projected onto the second projection surface.

According to a fifth aspect of the present disclosure, there is provided an information processing method including: acquiring a radiographic image captured by irradiating a breast compressed by a compression member with radiation; generating a projection image, which includes guide information serving as a guide in a case in which the breast is compressed and is capable of identifying whether the guide information is related to a right breast or a left breast, on the basis of a shape of the breast in the compressed state indicated by the radiographic image; and controlling an image projection unit which projects the projection image onto a first projection surface of the compression member such that the projection image is projected onto the first projection surface.

According to a sixth aspect of the present disclosure, there is provided an information processing program that causes a computer to perform a process including: acquiring a radiographic image captured by irradiating a breast compressed by a compression member with radiation; generating a projection image, which includes guide information serving as a guide in a case in which the breast is compressed and is capable of identifying whether the guide information is related to a right breast or a left breast, on the basis of a shape of the breast in the compressed state indicated by the radiographic image; and controlling an image projection unit which projects the projection image onto a first projection surface of the compression member such that the projection image is projected onto the first projection surface.

According to the present disclosure, it is possible to improve the efficiency of an imaging operation in mammography.

DETAILED DESCRIPTION

Hereinafter, embodiments of the present disclosure will be described in detail with reference to the drawings. In addition, each of the embodiments does not limit the present disclosure.

First Embodiment

Figure 1:
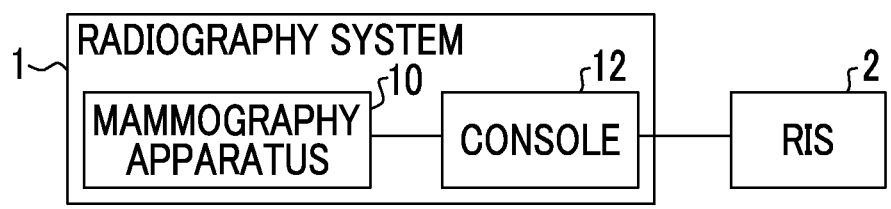
FIG. 1 is a diagram schematically illustrating an example of the overall configuration of a radiography system according to each embodiment.

First, an example of the overall configuration of a radiography system according to this embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12. The mammography apparatus 10 according to this embodiment is an example of a radiography apparatus according to the present disclosure. Further, the console 12 according to this embodiment is an example of an information processing device according to the present disclosure.

Figure 2:
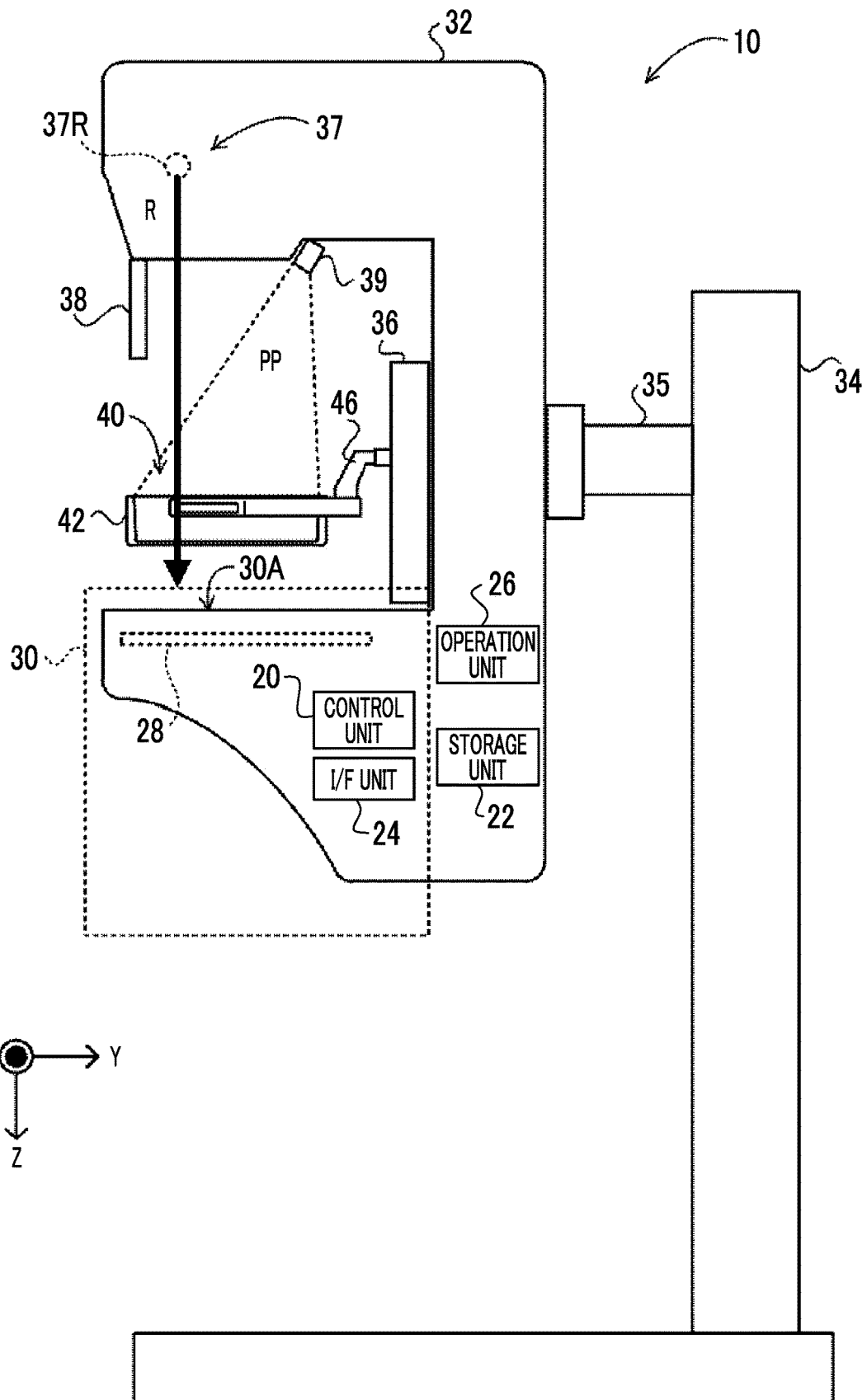
FIG. 2 is a side view illustrating an example of the outward appearance of a mammography apparatus according to each embodiment.

First, the mammography apparatus 10 according to this embodiment will be described. FIG. 2 is a side view illustrating an example of the outward appearance of the mammography apparatus 10 according to this embodiment. In addition, FIG. 2 illustrates an example of the outward appearance of the mammography apparatus 10 as viewed from the right side of a subject.

The mammography apparatus 10 according to this embodiment irradiates the breast of the subject as an object with radiation R (for example, X-rays) to capture a radiographic image of the breast. In addition, the mammography apparatus 10 may be an apparatus that captures the image of a breast of the subject not only in a state in which the subject is standing (standing state) but also in a state in which the subject is sitting, for example, on a chair (including a wheelchair) (sitting state).

As illustrated in FIG. 2, the mammography apparatus 10 according to this embodiment comprises a control unit 20, a storage unit 22, and an interface (I/F) unit 24 which are provided in an imaging table 30. The control unit 20 controls the overall operation of the mammography apparatus 10 under the control of the console 12. The control unit 20 comprises a central processing unit (CPU), a read only memory (ROM), and a random access memory (RAM) which are not illustrated. For example, various programs including an imaging processing program which is executed by the CPU and is used to perform control related to the capture of radiographic images are stored in the ROM in advance. The RAM temporarily stores various kinds of data.

For example, image data of the radiographic image captured by a radiation detector 28 and various other kinds of information are stored in the storage unit 22. Examples of the storage unit 22 include a hard disk drive (HDD) and a solid state drive (SSD).

The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

The operation unit 26 is provided as plural switches in, for example, the imaging table 30 of the mammography apparatus 10. Further, the operation unit 26 may be provided as a touch panel switch or may be provided as a foot switch that is operated by a user's feet.

As illustrated in FIG. 2, the radiation detector 28 is disposed in the imaging table 30. In the mammography apparatus 10 according to this embodiment, in a case in which imaging is performed, the breast of the subject is positioned on an imaging surface 30A of the imaging table 30 by a user such as a doctor or a radiology technician. The radiation detector 28 detects the radiation R transmitted through the breast and the imaging table 30, generates a radiographic image on the basis of the detected radiation R, and outputs image data indicating the generated radiographic image. In addition, the type of the radiation detector 28 is not particularly limited. For example, the radiation detector 28 may be an indirect-conversion-type radiation detector that converts the radiation R into light and converts the converted light into charge or a direct-conversion-type radiation detector that directly converts the radiation R into charge.

A radiation emitting unit 37 comprises a radiation source 37R. As illustrated in FIG. 2, the radiation emitting unit 37 is provided in an arm portion 32 together with the imaging table 30 and a compression unit 36. The radiation emitting unit 37 according to this embodiment is configured such that an irradiation field can be changed. The irradiation field may be changed, for example, by the operation of the operation unit 26 by the user or by the control unit 20 according to the type of an attached compression plate 40.

At least one projector 39, which is an example of an image projection unit according to the present disclosure, is provided at a position of the arm portion 32 which is away from the subject below the radiation emitting unit 37. The projector 39 projects a projection image PP onto a projection surface of the compression plate 40 under the control of the console 12. A display image corresponding to the projection image PP is displayed on the projection surface of the compression plate 40 by the projection of the projection image PP by the projector 39. The projection image PP includes guide information which will be described below. The projection surface is at least one surface that constitutes the compression plate 40. Known projectors, such as a liquid crystal projector, a Digital Light Processing (DLP) (registered trademark) projector, and a laser projector, can be used as the projector 39. In addition, plural projectors 39 that can project the projection image PP onto plural projection surfaces of the compression plate 40 may be provided. Further, for example, a mirror for changing the projection direction of the projector 39 may be provided.

A face guard 38 is attachably and detachably provided at a position of the arm portion 32 which is close to the subject below the radiation emitting unit 37. The face guard 38 is a protective member for protecting the subject from the radiation R emitted from the radiation source 37R.

As illustrated in FIG. 2, the mammography apparatus 10 according to this embodiment comprises the arm portion 32, a base 34, and a shaft portion 35. The arm portion 32 is held by the base 34 so as to be movable in an up-down direction (Z-axis direction). The shaft portion 35 connects the arm portion 32 to the base 34. In addition, the arm portion 32 can be relatively rotated with respect to the base 34, using the shaft portion 35 as a rotation axis.

Each of the arm portion 32, the imaging table 30, and the compression unit 36 can be relatively rotated with respect to the base 34, using the shaft portion 35 as a rotation axis. In this embodiment, engagement portions (not illustrated) are provided in each of the base 34, the arm portion 32, the imaging table 30, and the compression unit 36. The state of the engagement portions is switched to connect each of the arm portion 32, the imaging table 30, and the compression unit 36 to the base 34. The arm portion 32, the imaging table 30, and the compression unit 36 connected to the shaft portion 35 are integrally rotated on the shaft portion 35.

The compression unit 36 is provided with a compression plate driving unit (not illustrated) that moves the compression plate 40 in the up-down direction (Z-axis direction). The compression plate 40 according to this embodiment has a function of compressing the breast of the subject. A support portion 46 of the compression plate 40 is detachably attached to the compression plate driving unit and is moved in the up-down direction (Z-axis direction) by the compression plate driving unit to compress the breast of the subject between the compression plate 40 and the imaging table 30. The compression plate 40 according to this embodiment is an example of a compression member according to the present disclosure.

There are plural types of compression plates 40 that can be attached to the mammography apparatus 10 according to this embodiment. In this example, the compression plate 40 compresses the entire breast. However, the present disclosure is not limited thereto. For example, a compression plate 40 that compresses a portion of the breast may be used. In other words, the compression plate 40 may be smaller than the breast. For example, as the compression plate 40, a compression plate 40 for so-called spot imaging that captures a radiographic image of only the region in which a lesion is present is known. Further, other types of compression plates 40 include, for example, a compression plate corresponding to the size of the breast, a compression plate for axillary imaging, and a compression plate for enlargement imaging.

As a specific example, three types of compression plates 40A to 40C that can be attached to the mammography apparatus 10 according to this embodiment will be described with reference to FIGS. 3 to 5, respectively. Hereinafter, in a case in which the compression plates 40A to 40C are generically referred to regardless of the type, they are simply referred to as "compression plates 40".

Figure 3:
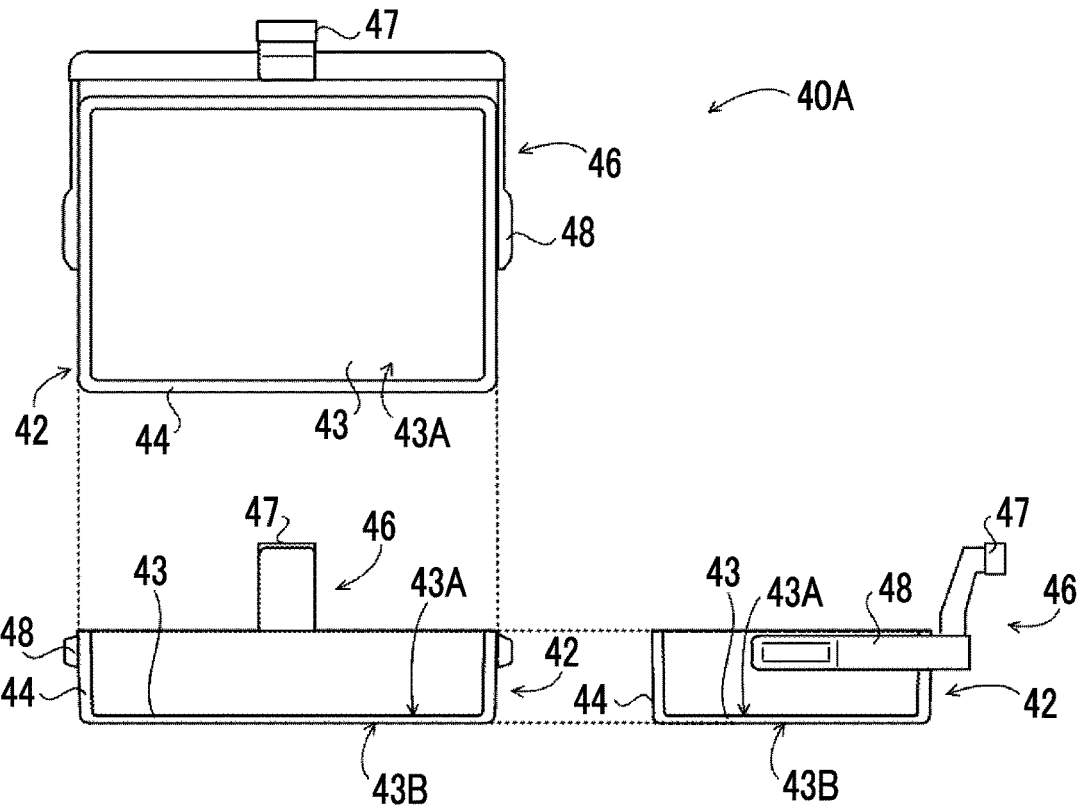
FIG. 3 is a three-view diagram illustrating an example of a compression plate.

FIG. 3 is a three-view diagram illustrating an example of the compression plate 40A according to this embodiment. The compression plate 40A is a standard-size compression plate that is mainly used outside Japan. The three-view diagram illustrated in FIG. 3 includes a plan view (top view) of the compression plate 40A viewed from the upper side (from the radiation emitting unit 37), a side view of the compression plate 40A viewed from the subject, and a side view of the compression plate 40A viewed from the right side of the subject. As illustrated in FIG. 3, the compression plate 40A according to this embodiment includes a compression portion 42 and a support portion 46.

The compression portion 42 is formed in a concave shape in a cross-sectional view in which a bottom portion 43 is surrounded by a wall portion 44. In the bottom portion 43, the thickness of a plate having a contact surface 43B that comes into contact with the breast of the subject is substantially constant, and an upper surface 43A that faces the radiation source 37R is flat and has a substantially uniform height. Further, the wall portion 44 is relatively high and has a substantially uniform height.

It is preferable that the compression portion 42 is optically transparent in order to check positioning or a compressed state in the compression of the breast. In addition, the compression portion 42 is made of a material having high transmittance for the radiation R. Specific examples of the material are resins, such as polycarbonate (PC), polyethylene terephthalate (PET), acrylic, and polypropylene (PP). However, the material is not particularly limited.

The support portion 46 is an example of a support member according to the present disclosure and includes an attachment portion 47 and an arm 48. The attachment portion 47 has a function of attaching the compression plate 40 to the mammography apparatus 10, specifically, the compression plate driving unit in the compression plate 40. The arm 48 has a function of supporting the compression portion 42.

Figure 4:
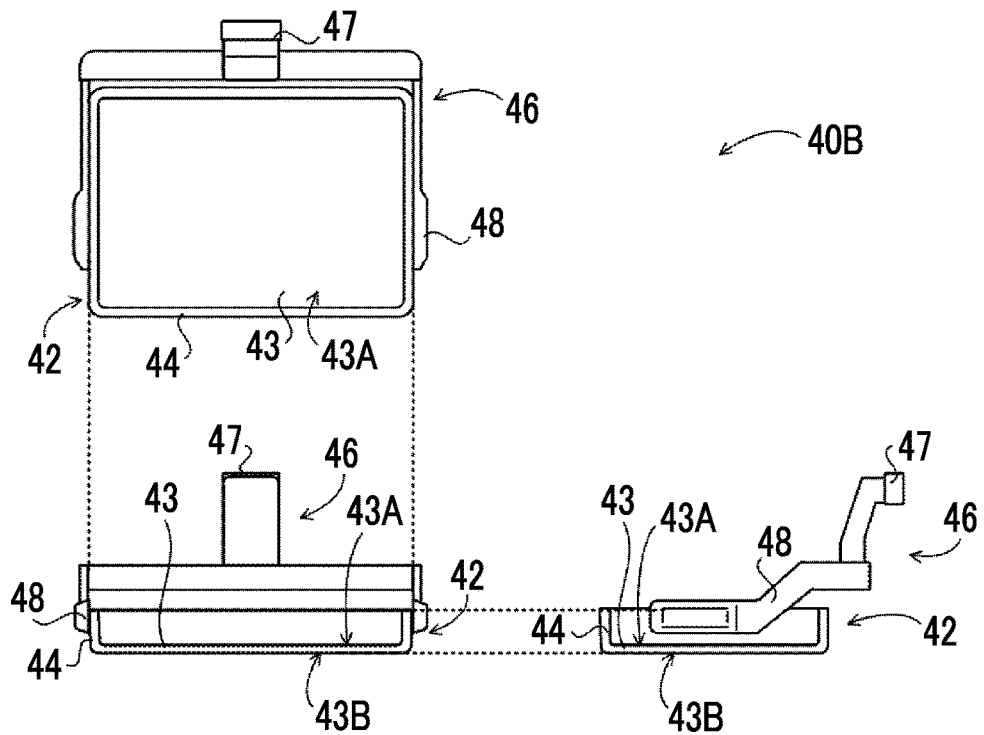
FIG. 4 is a three-view diagram illustrating an example of a compression plate.

FIG. 4 is a three-view diagram illustrating an example of the compression plate 40B according to this embodiment. The compression plate 40B is a compression plate having a smaller size than the compression plate 40A that is mainly used in Japan and is suitable for Japanese people who tend to have smaller breasts than foreigners. The three-view diagram illustrated in FIG. 4 includes a plan view (top view) of the compression plate 40B viewed from the upper side (from the radiation emitting unit 37), a side view of the compression plate 40B viewed from the subject, and a side view of the compression plate 40B viewed from the right side of the subject. As illustrated in FIG. 4, the compression plate 40B according to this embodiment includes a compression portion 42 and a support portion 46, similarly to the compression plate 40A. The compression plate 40B has a smaller bottom portion 43 and a lower wall portion 44 than the compression plate 40A illustrated in FIG. 3. Further, the support portion 46 includes an arm 48 having a different shape. The other configurations are the same as those of the compression plate 40A.

Figure 5:
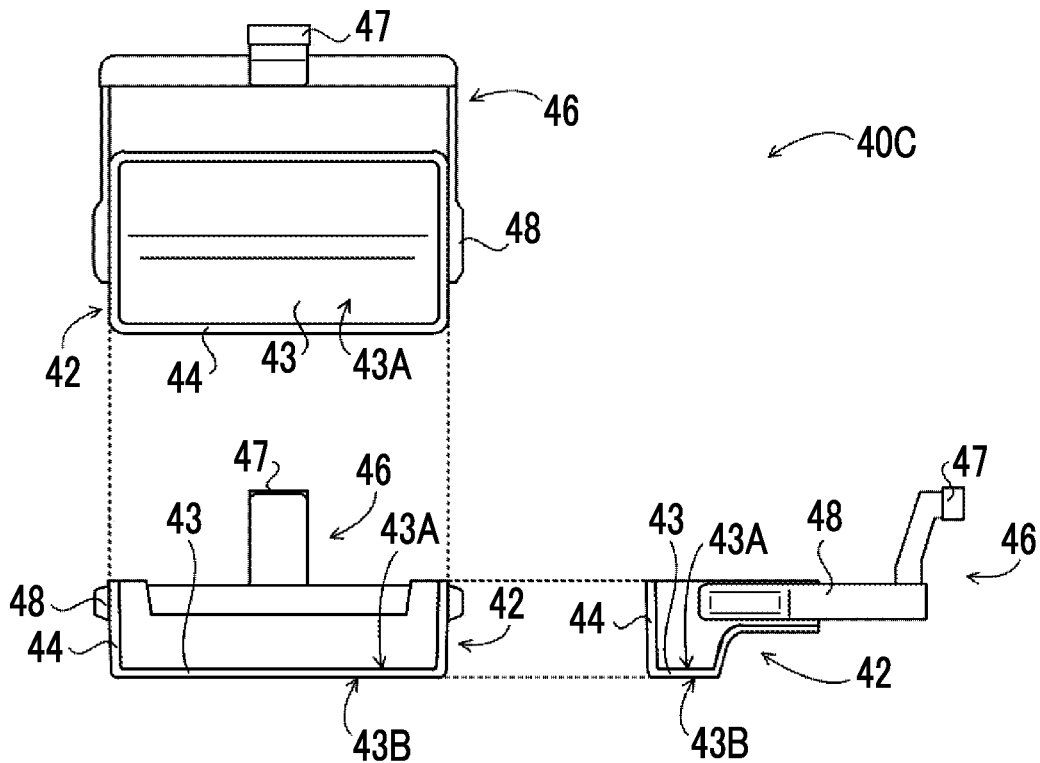
FIG. 5 is a three-view diagram illustrating an example of a compression plate.

FIG. 5 is a three-view diagram illustrating an example of the compression plate 40C according to this embodiment. The compression plate 40C is a compression plate for a small breast and has a shape that makes it easy for a radiographer to position and compress the breast. The three-view diagram illustrated in FIG. 5 includes a plan view (top view) of the compression plate 40C viewed from the upper side (from the radiation emitting unit 37), a side view of the compression plate 40C viewed from the subject, and a side view of the compression plate 40C viewed from the right side of the subject. As illustrated in FIG. 5, the compression plate 40C according to this embodiment includes a compression portion 42 and a support portion 46, similarly to the compression plates 40A and 40B. The compression plate 40C includes a bottom portion 43 which is not flat and in which a part close to an attachment portion 47 is higher than a part close to the chest wall (a part away from the attachment portion 47). Further, the height of a wall portion 44 is not uniform. In the wall portion 44, the height of a part close to the chest wall is lower than the height of the other parts.

In accordance with the above, different types of compression plates 40 are prepared according to, for example, the physique of the subject (for example, the size of the breast) and the type of imaging (for example, enlargement imaging and spot imaging) and can be attached to and detached from the mammography apparatus 10. Therefore, the mammography apparatus 10 according to this embodiment acquires identification information for identifying the type of the compression plate 40.

For example, plural pins whose disposition varies depending on the type of the compression plate 40 may be provided as the identification information in the attachment portion 47 of the compression plate 40, and the identification information may be read by a sensor that can detect the disposition of the pins provided in the mammography apparatus 10. In addition, for example, a detection marker corresponding to the type of the compression plate 40 may be provided as identification information at any position of the compression plate 40, and the identification information may be read by a sensor such as a photointerrupter that can detect each bit of the detection marker provided in the mammography apparatus 10. Further, for example, the mammography apparatus 10 may store a table, in which the identification information and weight of the compression plate 40 are associated with each other, in the storage unit 22 in advance, and the weight of the compression plate 40 measured by a sensor that can detect the weight may be collated with the table to acquire the identification information.

Next, the console 12 according to this embodiment will be described. The console 12 has a function of controlling the mammography apparatus 10 using, for example, an imaging order and various kinds of information acquired from a radiology information system (RIS) 2 through a wireless local area network (LAN) or the like and instructions input by the user through an operation unit 56 or the like.

The imaging order includes, for example, subject information, such as the name, sex, and date of birth of the subject whose image is to be captured, and an imaging item to be captured. For example, the imaging item is the designation of various types of imaging, such as cranio-caudal (CC) imaging, medio-lateral oblique (MLO) imaging, enlargement imaging, and spot imaging, for each of the left and right breasts.

Figure 6:
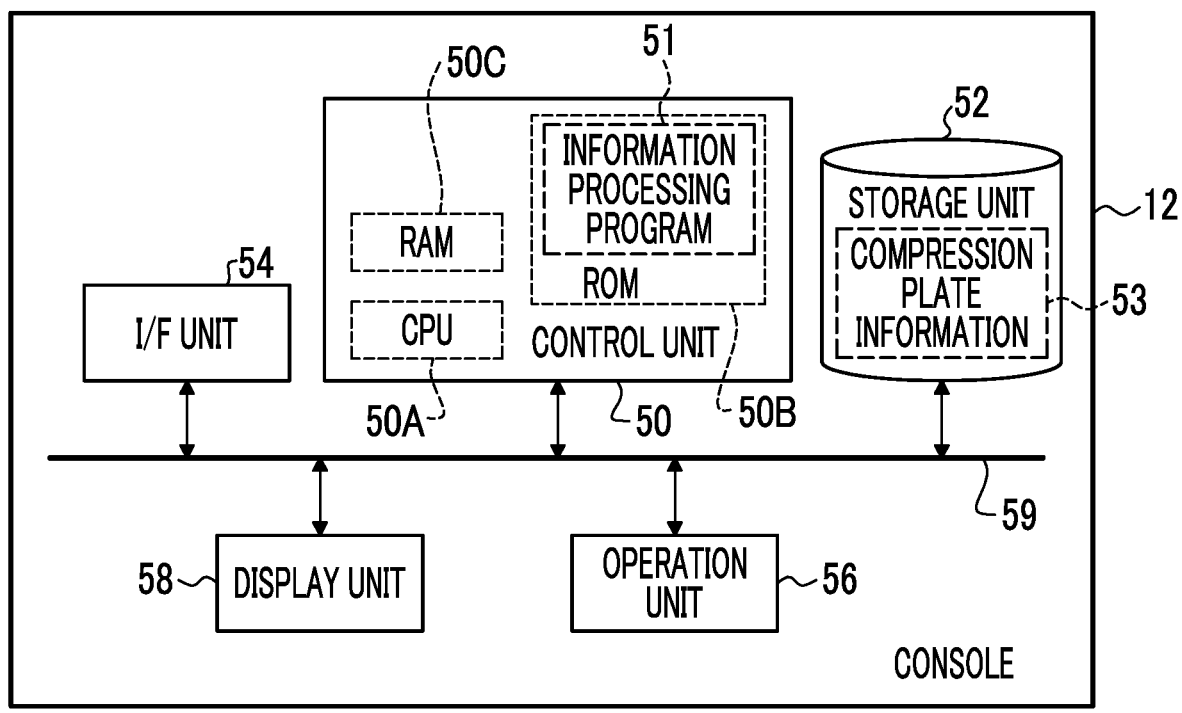
FIG. 6 is a block diagram illustrating an example of the hardware configuration of a console according to each embodiment.

For example, the console 12 according to this embodiment is a server computer. As illustrated in FIG. 6, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including an information processing program 51 (which will be described below) executed by the CPU 50A are stored in the ROM 50B in advance. The RAM 50C temporarily stores various kinds of data. The CPU 50A according to this embodiment is an example of a processor according to the present disclosure, and the ROM 50B according to this embodiment is an example of a memory according to the present disclosure.

For example, the image data of the radiographic image captured by the mammography apparatus 10, compression plate information 53, and various other kinds of information are stored in the storage unit 52. An HDD or an SSD is given as a specific example of the storage unit 52. The image data of the radiographic image is stored so as to be associated with the imaging order.

In addition, imaging information is given to the image data of the radiographic image. For example, the imaging information is at least one of subject information indicating the subject pertaining to the breast as an object to be imaged, radiographer information indicating the radiographer who performs imaging, date information indicating the date of imaging, radiographic image size information indicating the size of the radiographic image, or angle information indicating the angle at which the image of the breast is captured. The radiographer is, for example, a user such as a doctor or a radiology technician. The angle at which the image of the breast is captured is represented by, for example, the rotation angle of the arm portion 32 with respect to the base 34, is 0 degrees in the case of CC imaging, and is equal to or greater than 45 degrees and less than 90 degrees in the case of MLO imaging.

Figures 7, 8:
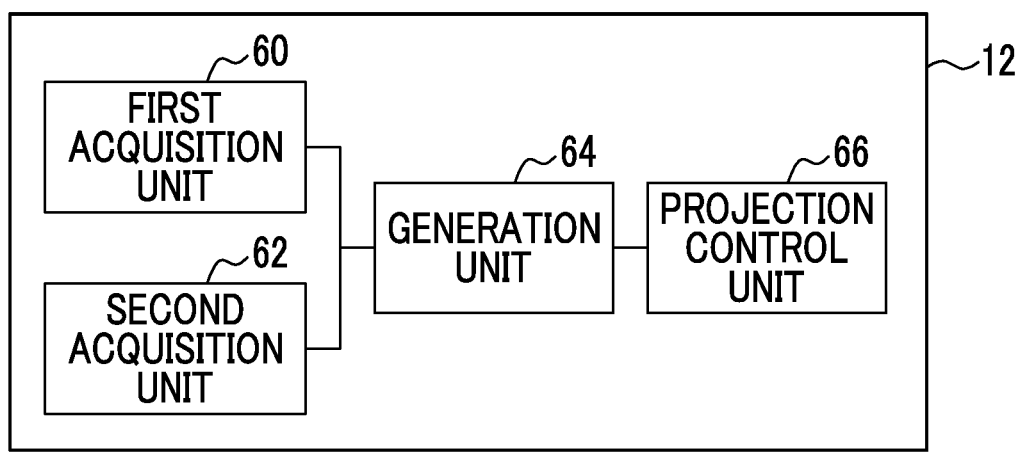
FIG. 7 is a diagram illustrating an example of compression plate information.
FIG. 8 is a functional block diagram illustrating an example of the functions of the console according to each embodiment.

FIG. 7 illustrates an example of the compression plate information 53. As illustrated in FIG. 7, the compression plate information 53 includes identification information assigned to each type of compression plate 40, information related to the size of the projection surface of the compression plate 40 (hereinafter, referred to as "projection surface size information"), and the size of the irradiation field suitable for the compression plate 40 which are associated with each other.

The operation unit 56 is used by the user to input, for example, instructions which are related to the capture of a radiographic image and include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information between the mammography apparatus 10 and the RIS 2 using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

FIG. 8 is a functional block diagram illustrating an example of the configuration of the console 12 according to this embodiment. As illustrated in FIG. 8, the console 12 comprises a first acquisition unit 60, a second acquisition unit 62, a generation unit 64, and a projection control unit 66. For example, in the console 12 according to this embodiment, the CPU 50A of the control unit 50 executes the information processing program 51 stored in the ROM 50B to function as the first acquisition unit 60, the second acquisition unit 62, the generation unit 64, and the projection control unit 66.

The first acquisition unit 60 acquires the projection surface size information indicating the size of the projection surface of the compression plate 40 in the mammography apparatus 10 that irradiates the breast compressed by the compression plate 40 with the radiation R to capture a radiographic image. Specifically, the first acquisition unit 60 acquires the identification information of the compression plate 40 identified by the mammography apparatus 10, collates the identification information with the compression plate information 53 (see FIG. 7) in the storage unit 52, and acquires the projection surface size information of the compression plate 40 attached to the mammography apparatus 10.

The second acquisition unit 62 acquires the radiographic image of the breast captured in the compressed state. For example, the second acquisition unit 62 acquires the radiographic image from the storage unit 52. In addition, the present disclosure is not limited thereto. For example, the radiographic images stored in the storage unit 22 of the mammography apparatus 10 may be acquired through the I/F unit 54, or the radiographic images stored in other consoles or various external devices may be acquired. In addition, the second acquisition unit 62 acquires radiographic image size information indicating the size of the acquired radiographic image.

Further, in a case in which there are plural radiographic images, the second acquisition unit 62 selects a radiographic image satisfying predetermined conditions from the plurality of radiographic images on the basis of the imaging information given to the radiographic images. A specific example of the conditions is described below. Only one of the following conditions may be used, or plural conditions may be combined. In addition, priority may be determined for each condition.

For example, it is assumed that subject information is given as the imaging information to each of the plurality of radiographic images. In this case, the second acquisition unit 62 uses, as a condition, the selection of a radiographic image to which subject information indicating a designated subject is given from the plurality of radiographic images. For example, it is preferable that a skin line image (which will be described in detail below) generated by the generation unit 64 is created on the basis of the radiographic image of the same subject as that which is the current object to be imaged. Therefore, the second acquisition unit 62 acquires the information of the subject as the current object to be imaged on the basis of the imaging order and selects the past radiographic image to which the subject information related to the same subject is given. Further, it is preferable to particularly select a radiographic image including the breast on the same side (the left breast or the right breast) as the breast as the object to be imaged among the plurality of radiographic images related to the same subject. Furthermore, in a case in which there is no radiographic image including the breast on the same side, a radiographic image including the breast on the other side may be reversed in a left-right direction and then used.

In addition, for example, it is assumed that the radiographer information is given as the imaging information to each of the plurality of radiographic images. In this case, the second acquisition unit 62 uses, as a condition, the selection of a radiographic image, to which radiographer information indicating a designated radiographer is given, from the plurality of radiographic images. For example, since a breast positioning method may vary depending on the radiographer, it is preferable to create the skin line image on the basis of the radiographic image taken by the same radiographer as the radiographer performing the current imaging. Therefore, the second acquisition unit 62 acquires the information of the radiographer who performs the current imaging and selects the past radiographic image to which the radiographer information related to the same radiographer is given.

Further, for example, it is assumed that date information is given as the imaging information to each of the plurality of radiographic images. In this case, the second acquisition unit 62 uses, as a condition, the selection of a radiographic image to which date information indicating a designated date is given from the plurality of radiographic images. For example, in some cases, the subject becomes thin or fat with the passage of days, which results in a change in the shape such as the size of the breast. It is preferable to create the skin line image on the basis of the radiographic image of the breast having a shape similar to that of the breast whose image is currently captured. Therefore, the second acquisition unit 62 selects the past radiographic image to which date information within a predetermined period close to the date when the current imaging is performed is given.

Further, for example, it is assumed that radiographic image size information is given as the imaging information to each of the plurality of radiographic images. In this case, the second acquisition unit 62 uses, as a condition, the selection of a radiographic image to which radiographic image size information indicating a size within a designated range is given from the plurality of radiographic images. For example, it is preferable to create the skin line image on the basis of a radiographic image having a size that is equal to or close to the size of the radiographic image which is currently captured. In addition, in some cases, the radiographic image captured with a small irradiation field as in spot imaging or the like is unsuitable for generating the skin line image. Therefore, the second acquisition unit 62 selects the past radiographic image to which radiographic image size information indicating a size that is equal to or close to the size of the radiographic image that is currently captured and is equal to or greater than a predetermined size is given.

In addition, as illustrated in FIG. 7, the size of the compression plate 40 and the size of the irradiation field, that is, the radiographic image are associated with each other on a one-to-one basis. Therefore, the second acquisition unit 62 may select a radiographic image using information related to the size of the compression plate 40 used for imaging, instead of the radiographic image size information.

Further, for example, it is assumed that angle information is given as the imaging information to each of the plurality of radiographic images. In this case, the second acquisition unit 62 uses, as a condition, the selection of a radiographic image to which angle information indicating an angle within a designated range is given from the plurality of radiographic images. For example, the shape of the compressed breast changes as the imaging angle changes. Therefore, it is preferable to create the skin line image on the basis of the radiographic image captured at an angle that is equal to or close to the angle at which the current imaging is performed. Therefore, the second acquisition unit 62 selects the past radiographic image to which angle information indicating an angle that is within a predetermined range and is equal to or close to the angle at which the current imaging is performed is given.

In addition, the second acquisition unit 62 may perform control to issue a warning in a case in which there is no radiographic image satisfying each of the predetermined conditions. Specifically, for example, after the generation and projection of the skin line image, which will be described below, are performed on the basis of any radiographic image that does not satisfy the conditions, a warning indicating that the reliability of the skin line image is low may be displayed on the display unit 58.

Further, the second acquisition unit 62 may perform control to stop the projection of the projection image PP in a case in which there is no radiographic image satisfying each of the predetermined conditions. Specifically, a skin line image generation and projection process which will be described below may be stopped.

The generation unit 64 generates the projection image PP having a size corresponding to the projection surface size information acquired by the first acquisition unit 60. Specifically, the generation unit 64 generates the projection image PP including guide information that serves as a guide in a case in which the breast is compressed on the basis of the shape of the breast in the compressed state indicated by the radiographic image selected by the second acquisition unit 62. The guide information is information indicating at least a portion of the periphery of the breast in the compressed state and is, for example, a skin line image indicating the periphery of the breast compressed by the compression plate 40, an image indicating the position of the nipples, or the captured radiographic image of the breast.

A specific example of a process for generating the projection image PP having a size corresponding to the projection surface size information will be described with reference to FIGS. 9 and 10. First, the generation unit 64 compares the size of a radiographic image RG1 indicated by the radiographic image size information acquired by the second acquisition unit 62 with the size of the projection surface indicated by the projection surface size information acquired by the first acquisition unit 60 to determine which of the two sizes is larger.

Figure 9:
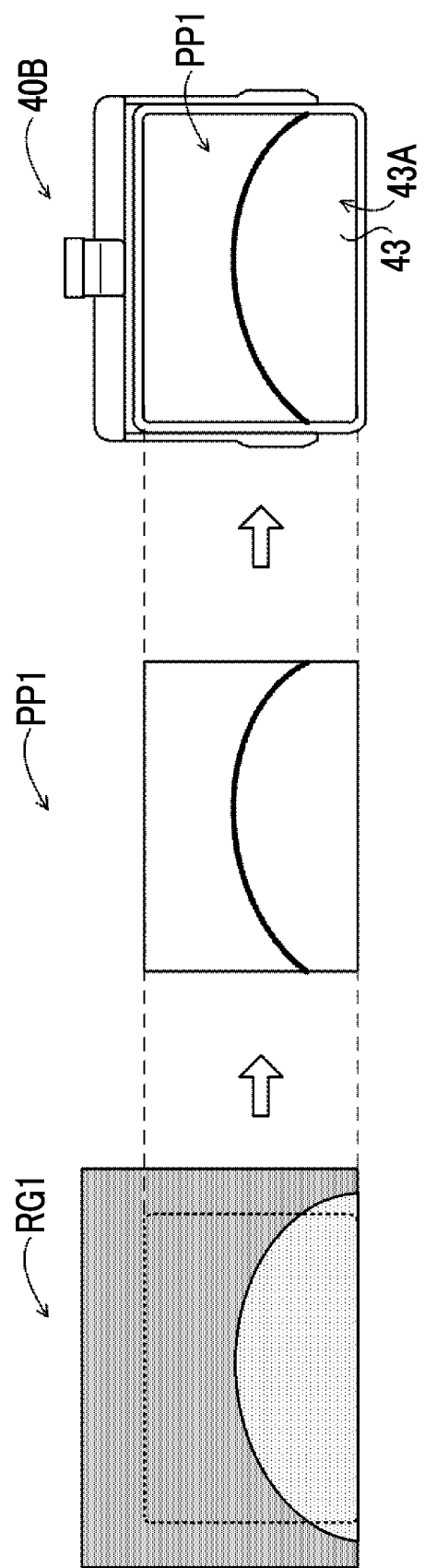
FIG. 9 is a diagram illustrating a projection image generation process according to a first embodiment.

FIG. 9 is a diagram illustrating a process in a case in which a projection image PP1 to be projected onto the projection surface (upper surface 43A) of the compression plate 40B which is smaller than the radiographic image RG1 is generated on the basis of the radiographic image RG1 acquired by the second acquisition unit 62. The projection image PP1 is an example of the projection image PP. FIG. 9 illustrates the radiographic image RG1 of the breast in the compressed state, the projection image PP1 including the skin line image generated on the basis of the shape of the breast in the compressed state indicated by the radiographic image RG1, and a state in which the projection image PP1 is projected onto the compression plate 40B. The skin line image is an example of guide information according to the present disclosure.

In a case in which the radiographic image RG1 is larger than the projection surface as in the example illustrated in FIG. 9, the generation unit 64 generates the projection image PP1 including the skin line image based on the shape of the breast indicated by a partial region of the radiographic image RG1 which corresponds to the size of the projection surface. That is, the generation unit 64 cuts a partial region of the radiographic image RG1 which corresponds to the size of the projection surface and generates the projection image PP1 including the skin line image on the basis of the cut image. It is preferable that the region to be cut is a partial region on the chest wall side as illustrated in FIG. 9. The reason is that, in many cases, an image including the chest wall side is captured in mammography. Further, it is preferable that the region to be cut is a partial region including the center of the shape of the breast included in the radiographic image RG1 in the left-right direction.

In addition, a method for generating the skin line image is not particularly limited. For example, the skin line image may be generated by dividing the radiographic image RG1 into a breast region and a blank region on the basis of the density of each pixel of the radiographic image RG1 and connecting the pixels which are the boundary points between the breast region and the blank region (see JP2010-051456A).

Figure 10:
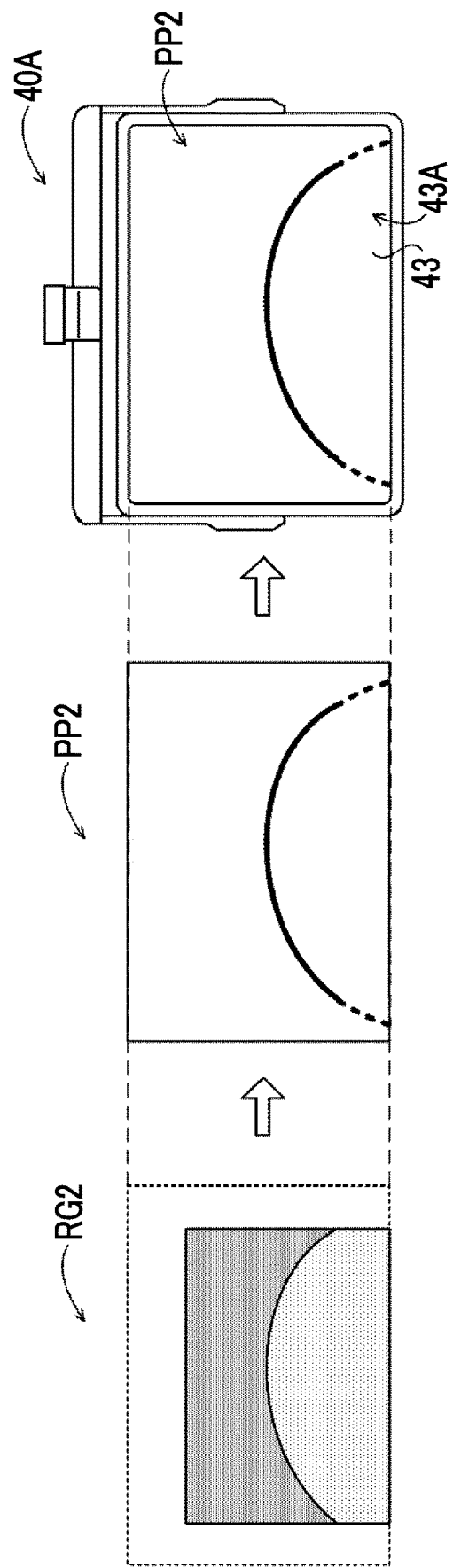
FIG. 10 is a diagram illustrating the projection image generation process according to the first embodiment.

On the other hand, FIG. 10 illustrates a process in a case in which a projection image PP2 to be projected onto the projection surface (upper surface 43A) of the compression plate 40A which is larger than a radiographic image RG2 acquired by the second acquisition unit 62 is generated on the basis of the radiographic image RG2. The projection image PP2 is an example of the projection image PP. FIG. 10 illustrates the radiographic image RG2 of the breast in the compressed state, the projection image PP2 including the skin line image generated on the basis of the shape of the breast in the compressed state indicated by the radiographic image RG2, and a state in which the projection image PP2 is projected onto the compression plate 40A.

In a case in which the radiographic image RG2 is smaller than the projection surface as in the example illustrated in FIG. 10, the generation unit 64 generates the projection image PP2 including the skin line image in which the shape of the breast outside the radiographic image RG2 has been complemented, on the basis of the shape of the breast indicated by the radiographic image RG2. A known image complementing method can be applied as the complementing method. For example, an extension line may be complemented on the basis of the curvature of the skin line image of a portion generated on the basis of the radiographic image RG2. Further, for example, a tangent line of the skin line image of the portion generated on the basis of the radiographic image RG2 may be complemented as an extension line. Furthermore, for example, the past skin line image similar to the skin line image of the portion generated on the basis of the radiographic image RG2 may be used.

In addition, the generation unit 64 may generate the projection image PP including the skin line image based on the shape of the breast indicated by an image obtained by enlarging or reducing the radiographic image according to the projection surface size information. For example, an enlargement and reduction ratio may be predetermined for each combination of the radiographic image size information and the projection surface size information.

A case in which the projection image PP to be projected onto the compression plate for spot imaging is generated on the basis of the radiographic image captured by the compression plate 40A with a standard size will be described as an example. Imaging is performed in a state in which not the entire breast but only the region of interest of the breast is compressed by the compression plate for spot imaging. In this case, compression pressure is applied only to the region of interest such that the part to be compressed can be compressed thinner and flatter than that in a case in which the compression plate 40A with the standard size is used. In this case, it is preferable that a partial region of the radiographic image is not just cut according to the size of the projection surface, but the radiographic image is enlarged considering that the breast becomes thin and flat and the contour of the breast is enlarged.

In addition, in the process of generating the projection image PP including the guide information (skin line image) with the generation unit 64, the processing order of the generation of the guide information based on the radiographic image and the generation of the projection image PP having a size corresponding to the projection surface size information is not limited. For example, after the guide information is generated on the basis of the radiographic image, the guide information may be processed (for example, cut, complemented, enlarged, or reduced) on the basis of the projection surface size information. Further, for example, after the radiographic image is processed on the basis of the projection surface size information, the guide information may be generated on the basis of the processed radiographic image. Furthermore, for example, the processing order may vary depending on the type of processing such as cutting, complementing, enlargement, or reduction. Specifically, in a case in which the cutting process (see FIG. 9) is performed, the guide information may be generated after the radiographic image is cut. In a case in which the complementing process (see FIG. 10) is performed, the guide information may be complemented after the guide information is generated.

The projection control unit 66 performs control to direct the projector 39, which projects the projection image PP onto the projection surface of the compression plate 40, to project the projection image PP generated by the generation unit 64 onto the projection surface.

Figure 11:
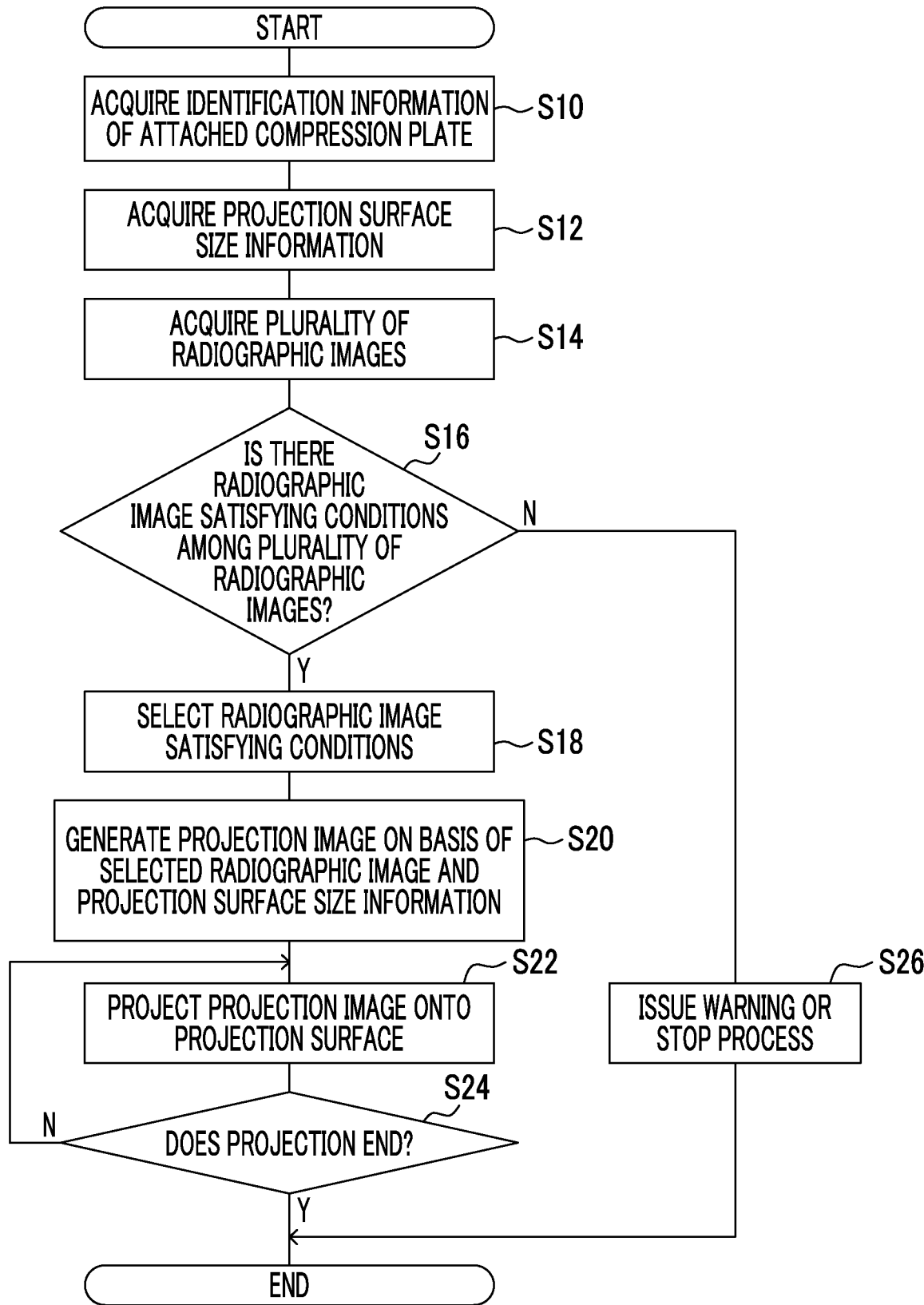
FIG. 11 is a flowchart illustrating an example of the flow of information processing in the console according to the first embodiment.

Next, the operation of the console 12 according to this embodiment will be described with reference to FIG. 11. For example, in a case in which the console 12 according to this embodiment receives an imaging order from the RIS 2 or the like, the CPU 50A of the control unit 50 executes the information processing program 51 stored in the ROM 50B to perform the information processing whose example is illustrated in FIG. 11. FIG. 11 is a flowchart illustrating an example of the flow of the information processing performed in the console 12 according to this embodiment.

In Step S10 of FIG. 11, the first acquisition unit 60 acquires the identification information of the compression plate 40 identified by the mammography apparatus 10. In Step S12, the first acquisition unit 60 collates the identification information of the compression plate 40 acquired in Step S10 with the compression plate information 53 and acquires the projection surface size information of the compression plate 40 attached to the mammography apparatus 10.

In Step S14, the second acquisition unit 62 acquires plural radiographic images captured in the past. In Step S16, the second acquisition unit 62 searches for a radiographic image satisfying the predetermined conditions from the plurality of radiographic images acquired in Step S14 on the basis of the imaging information given to the radiographic image. In a case in which there is a radiographic image satisfying the conditions (Y in Step S16), the second acquisition unit 62 selects the radiographic image satisfying the conditions in Step S18.

In Step S20, the generation unit 64 generates the projection image PP including the skin line image on the basis of the radiographic image selected in Step S18 and the projection surface size information acquired in Step S12. In Step S22, the projection control unit 66 performs control to project the projection image PP generated in Step S20 onto the projection surface of the compression plate 40. In Step S24, the projection control unit 66 determines whether or not to end the projection and returns to Step S22 in a case in which the projection is continued (N in Step S24). On the other hand, the process ends in a case in which the projection is ended (Y in Step S24). In addition, it is determined that the projection is ended at a predetermined timing such as the operation of the operation unit 56 by the user and the completion of the capture of the radiographic image.

On the other hand, in a case in which there is no radiographic image satisfying the conditions in Step S16 (N in Step S16), the second acquisition unit 62 performs control to issue a warning or control to stop the projection of the projection image PP in Step S26. Then, the process ends.

As described above, the console 12 according to this embodiment comprises the CPU 50A which corresponds to at least one processor. The CPU 50A acquires the projection surface size information indicating the size of the projection surface of the compression plate 40 in the mammography apparatus 10 that irradiates the breast compressed by the compression plate 40 with the radiation R to capture a radiographic image. Further, the CPU 50A generates the projection image PP having a size corresponding to the projection surface size information and performs control to direct the projector 39, which projects the projection image PP onto the projection surface of the compression plate 40, to project the projection image PP onto the projection surface. Therefore, it is possible to project the projection image PP having a size corresponding to the size of the compression plate 40 provided in the mammography apparatus 10.

In addition, in the above-described embodiment, the aspect in which an image including a skin line image is projected as the projection image PP has been described. However, the present disclosure is not limited thereto, and any image can be applied as the projection image PP. For example, the present disclosure includes an aspect in which an image including character information, such as compression pressure and the thickness of the breast, is projected according to the size of the projection surface of the compression plate 40.

Further, in the above-described embodiment, the aspect in which the generation unit 64 generates the skin line image on the basis of the radiographic image acquired by the second acquisition unit 62 has been described. However, the present disclosure is not limited thereto. For example, an external device may generate a skin line image for each radiographic image in advance, and the console 12 may acquire the skin line image. In this case, the generation unit 64 may generate an image obtained by cutting, complementing, enlarging, or reducing the acquired skin line image on the basis of the projection surface size information acquired by the first acquisition unit 60.

Second Embodiment

In the actual scene of mammography, the images of two left and right breasts of the same subject are generally captured. The user who performs imaging operates the console 12 to confirm the imaging order, and checks the breast whose image is to be captured, an imaging item (for example, CC imaging, MLO imaging, enlargement imaging, and spot imaging), and the order of imaging, and performs imaging using the mammography apparatus 10. In a case in which the mammography apparatus 10 and the console 12 are disposed at a distance and the user wants to reconfirm, for example, the imaging order indicating which of the image of the right breast and the image of the left breast is captured first, the user has to leave the mammography apparatus 10 once, which reduces the efficiency of the imaging operation.

Therefore, the generation unit 64 according to this embodiment generates the projection image PP, which includes guide information serving as a guide in a case in which the breast is compressed and can identify whether the guide information is related to the right breast or the left breast, on the basis of the shape of the breast in the compressed state indicated by the radiographic image. Further, the projection control unit 66 performs control to direct the projector 39 to project the projection image PP generated by the generation unit 64 onto a first projection surface. The first projection surface is one surface that constitutes the compression plate 40. In addition, as described above, the image data of the radiographic image is stored in the storage unit 52 so as to be associated with the imaging order. In addition, whether the guide information generated on the basis of the radiographic image is related to the right breast or the left breast is stored in the storage unit 52 so as to be associated with the imaging order. Hereinafter, the same configurations as those in the first embodiment are denoted by the same reference numerals, and the description thereof will not be repeated.

Figure 12:
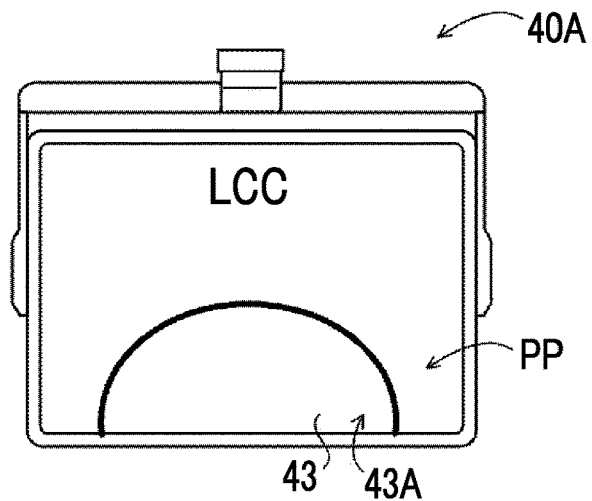
FIG. 12 is a diagram illustrating the compression plate onto which a skin line image of the left breast is projected in a second embodiment.
Figure 13:
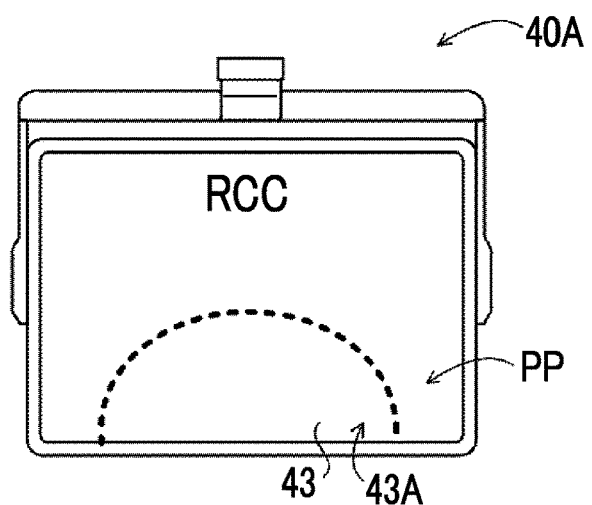
FIG. 13 is a diagram illustrating the compression plate onto which a skin line image of the right breast is projected in the second embodiment.
Figure 14:
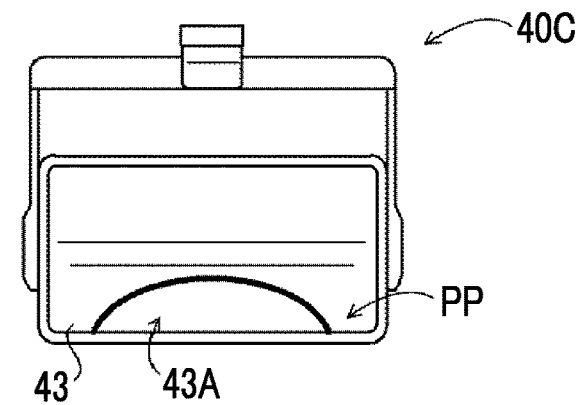
FIG. 14 is a diagram illustrating a compression plate for a small breast onto which the skin line image of the left breast is projected in the second embodiment.
Figure 15:
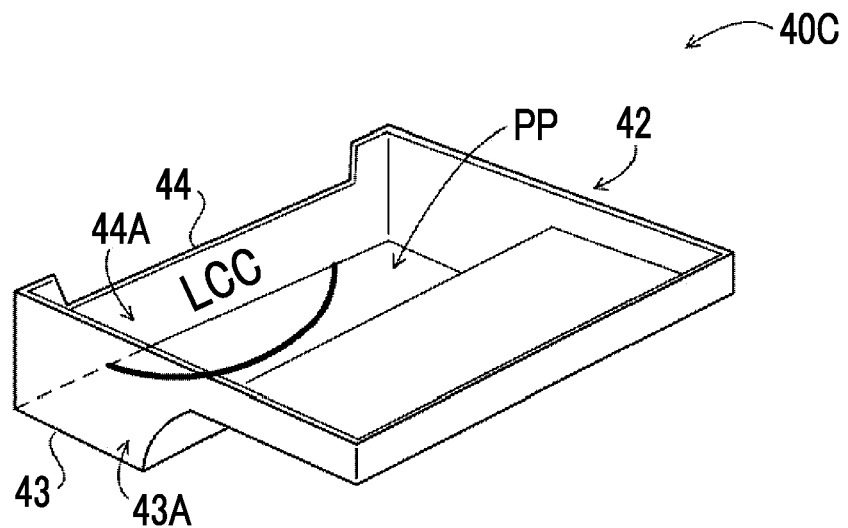
FIG. 15 is a diagram illustrating the compression plate for a small breast onto which the skin line image of the left breast is projected in the second embodiment.

A specific example of the "projection image PP that can identify whether the guide information is related to the right breast or the left breast" will be described with reference to FIGS. 12 to 15. FIGS. 12 and 13 are diagrams illustrating a state in which the projection image PP for CC imaging is projected onto the compression plate 40A with the standard size, and FIGS. 14 and 15 are diagrams illustrating a state in which the projection image PP for CC imaging is projected onto the compression plate 40C with a small breast. FIGS. 12 to 15 illustrate skin line images as examples of the guide information according to the present disclosure.

As illustrated in FIGS. 12 and 13, for example, the generation unit 64 may generate the projection image PP while changing a display aspect depending on whether the guide information is related to the right breast or the left breast. In this case, the projection control unit 66 performs control to project the projection image PP generated by the generation unit 64 onto the first projection surface (upper surface 43A). The display aspect includes, for example, a line type (a solid line, a broken line, and the like), a line thickness, and a line color in the guide information (skin line image). For example, the skin line image related to the left breast is represented by a solid line in FIG. 12, and the skin line image related to the right breast is represented by a broken line in FIG. 13.

Further, as illustrated in FIGS. 12 and 13, the generation unit 64 may generate the projection image PP including, for example, the guide information and left-right information indicating whether the guide information is related to the right breast or the left breast. In this case, the projection control unit 66 may perform control to project the projection image PP generated by the generation unit 64 onto the first projection surface (upper surface 43A). For example, FIG. 12 illustrates the left-right information of "LCC" which means CC imaging for the left breast, and FIG. 13 illustrates the left-right information of "RCC" which means CC imaging for the right breast.

On the other hand, there is a case in which the first projection surface (upper surface 43A) of the compression plate 40 is small and it is inappropriate to project the guide information and the left-right information onto one projection surface as illustrated in FIG. 14. In this case, the projector 39 may project an image on a second projection surface (an inner surface 44A of the wall portion 44) which is a surface different from the first projection surface of the compression plate 40, in addition to the first projection surface (upper surface 43A). In this case, as illustrated in FIG. 15, the projection control unit 66 performs control to direct the projector 39 to project the guide information onto the first projection surface (upper surface 43A) and to project the left-right information onto the second projection surface (inner surface 44A).

Figure 16:
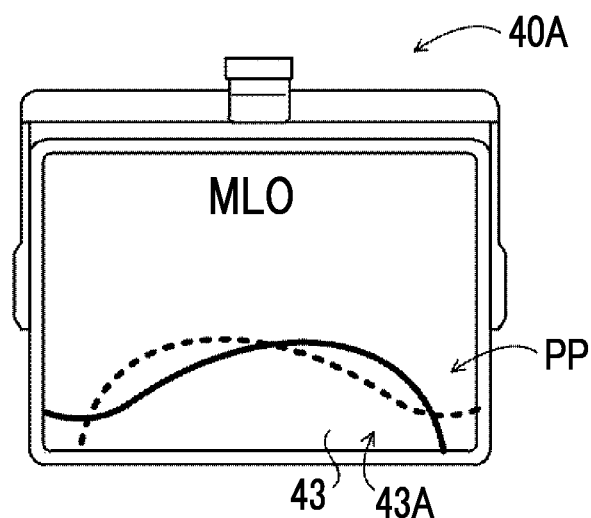
FIG. 16 is a diagram illustrating the compression plate onto which the skin line images of the left breast and the right breast are projected at the same time in the second embodiment.

In addition, in the MLO imaging, the image of a part including the axilla is captured. Therefore, as illustrated in FIG. 16, the generation unit 64 generates guide information (skin line image) indicating the shape of the axilla in addition to the shape of the breast. In this case, the position of the axilla is different between the right breast and the left breast. Therefore, the user can determine which breast the guide information is related to, without changing the display aspect depending on whether the guide information is related to the right breast or the left breast or without displaying the left-right information. Therefore, in the MLO imaging, as illustrated in FIG. 16, the generation unit 64 may generate the projection image PP including guide information related to each of the right breast and the left breast. That is, as illustrated in FIG. 16, the guide information related to each of the right breast and the left breast may be displayed on the first projection surface (upper surface 43A) at the same time.

However, it is preferable that the generation unit 64 changes the display aspect depending on whether the guide information is related to the right breast or the left breast in order to improve visibility as illustrated in FIG. 16. Further, in these cases, the projection control unit 66 may perform control to project the projection image PP including the guide information related to only one of the right breast and the left breast onto the first projection surface (upper surface 43A) in response to the operation of the operation unit 56 or the operation unit 26 by the user.

Figure 17:
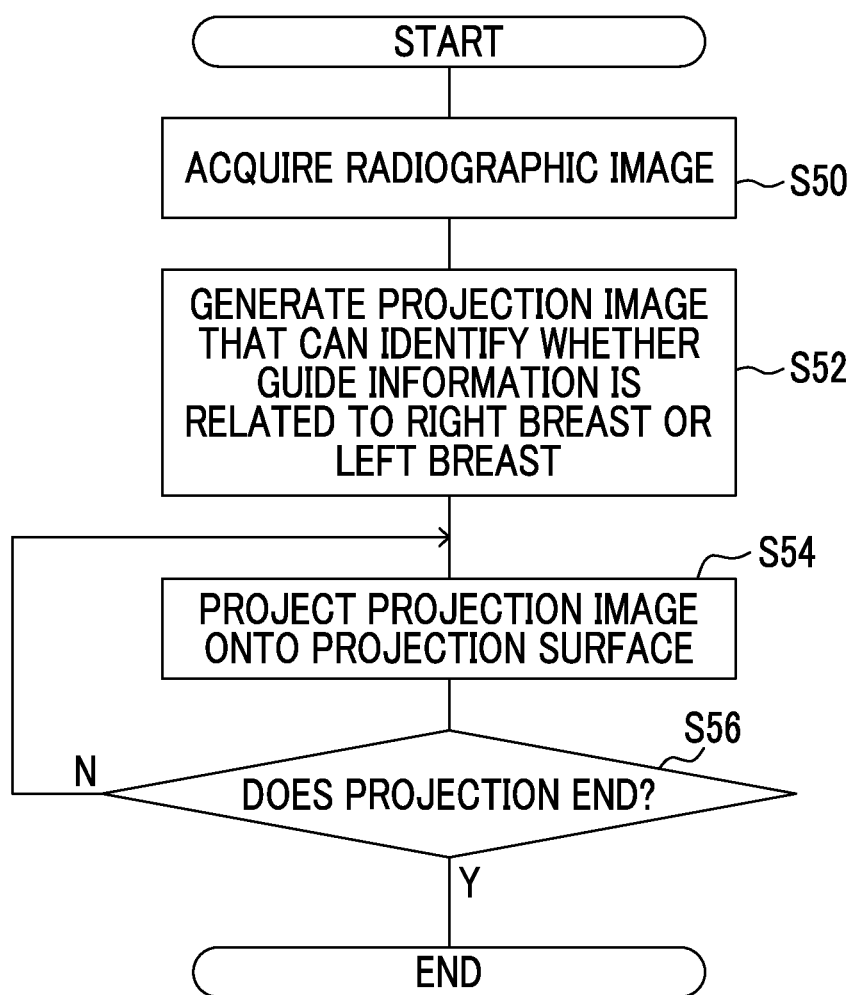
FIG. 17 is a flowchart illustrating an example of the flow of information processing in a console according to the second embodiment.

Next, the operation of the console 12 according to this embodiment will be described with reference to FIG. 17. For example, in a case in which the console 12 according to this embodiment receives an imaging order from the RIS 2 or the like, the CPU 50A of the control unit 50 executes the information processing program 51 stored in the ROM 50B to perform the information processing whose example is illustrated in FIG. 17. FIG. 17 is a flowchart illustrating an example of the flow of the information processing performed in the console 12 according to this embodiment.

In Step S50 of FIG. 17, the second acquisition unit 62 acquires a radiographic image. In Step S52, the generation unit 64 generates a projection image, which includes guide information and can identify whether the guide information is related to the right breast or the left breast, on the basis of the radiographic image. In Step S54, the projection control unit 66 performs control to project the projection image PP generated in Step S52 onto the projection surface of the compression plate 40. In Step S56, the projection control unit 66 determines whether or not to end the projection and returns to Step S54 in a case in which the projection is continued (N in Step S56). On the other hand, in a case in which the projection is ended (Y in Step S56), the process ends. In addition, it is determined that the projection is ended at a predetermined timing such as the operation of the operation unit 56 by the user and the completion of the capture of the radiographic image.

As described above, the console 12 according to this embodiment comprises the CPU 50A which corresponds to at least one processor. The CPU 50A acquires the radiographic image of the breast captured in the compressed state and generates the projection image PP, which includes the guide information serving as a guide in a case in which the breast is compressed and can identify whether the guide information is related to the right breast or the left breast, on the basis of the shape of the breast in the compressed state indicated by the radiographic image. Further, the CPU 50A performs control to direct the projector 39, which projects the projection image PP onto the first projection surface of the compression plate 40, to project the projection image PP onto the first projection surface. Therefore, the user can check whether to perform imaging for the right breast or the left breast while handling the mammography apparatus 10, and it is possible to improve the efficiency of the imaging operation in mammography.

In addition, the technology of this embodiment is not applied only to the aspect in which the projection image PP having a size corresponding to the size of the projection surface is projected as described in the first embodiment, but can also be executed independently. For example, the technology of this embodiment can be applied to any radiography system that projects the projection image PP including guide information, such as a skin line image, regardless of whether or not the size of the projection image PP is changed depending on the size of the projection surface.

Further, in the above-described embodiment, as illustrated in FIGS. 12, 13, and 17, the aspect in which the display aspect varies depending on the right breast or the left breast and the aspect in which the left-right information is displayed are combined with each other. However, the present disclosure is not limited thereto, and these aspects may be performed independently.

Configuration of Compression Plate 40 Capable of Projecting Light

The configuration of the compression plate 40 onto which the projection image PP can be projected by the projector 39 will be described as a configuration common to the first and second embodiments with reference to FIGS. 18 to 22. As described above, in this embodiment, the compression portion 42 of the compression plate 40 is configured to include a material that is optically transparent in order to perform positioning and to check the compressed state in the compression of the breast. In a case in which light is incident on a transparent object, most (for example, 90%) of the light is transmitted, and a portion (for example, 10%) of the light is specularly reflected from the surface of the object such that an incident angle and a reflection angle are equal to each other. In practice, light absorption occurs in the object, and scattering occurs at the interface of the object and in the object. However, they will be ignored here. Light reflected from the surface of the object enters the eyes, and the observer can see light projected onto the surface of the object. That is, even in the compression plate 40 configured to include a transparent material, in a case in which the projection image PP projected by the projector 39 is reflected from the projection surface of the compression plate 40 and the reflected light enters the eyes of the observer, the observer can visually recognize the image displayed on the projection surface.

Figure 18:
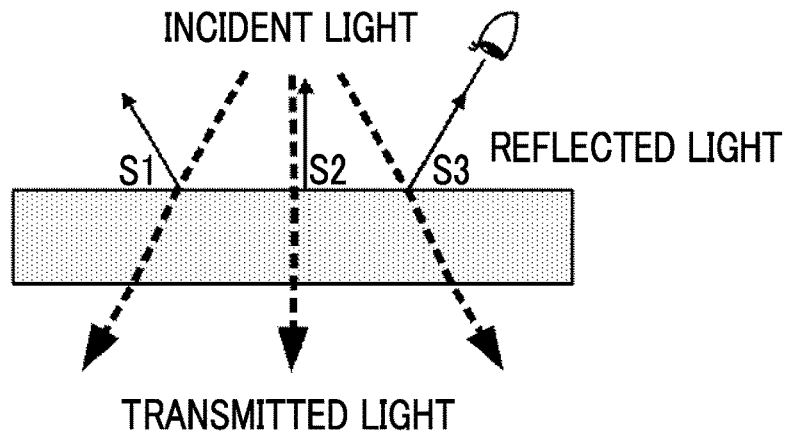
FIG. 18 is a diagram illustrating the principle of reflection from a smooth flat surface.
Figure 19:
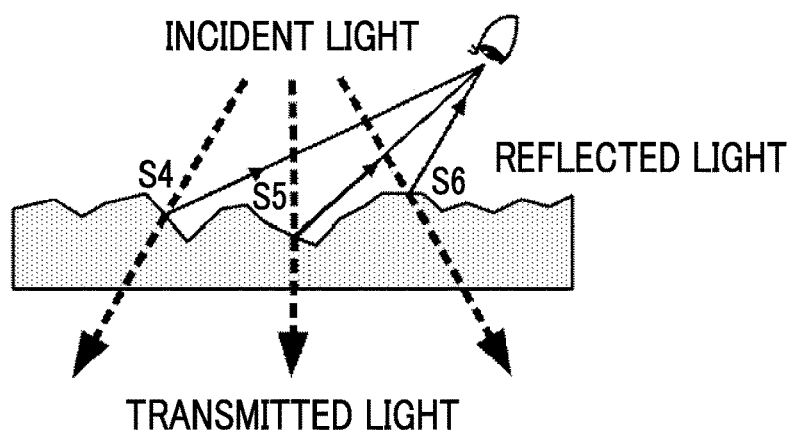
FIG. 19 is a diagram illustrating the principle of reflection from a roughened surface.
Figure 20:
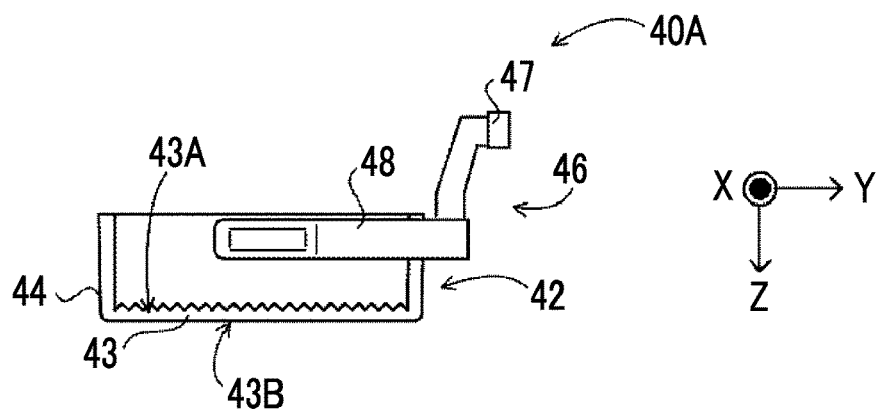
FIG. 20 is a diagram schematically illustrating an example of a compression plate having a roughened projection surface.

FIG. 18 is a diagram illustrating an example of the direction of the reflected light in a case in which incident light is incident on a smooth flat surface. FIG. 19 is a diagram illustrating an example of the direction of the reflected light in a case in which incident light is incident on an uneven surface. In FIGS. 18 and 19, three incident light components are illustrated as representatives. As illustrated in FIGS. 18 and 19, light incident on each of positions S1 to S6 on the surface of the object is specularly reflected, regardless of whether the surface of the object is a smooth flat surface or an uneven surface.

As illustrated in FIG. 18, in a case in which the surface of the object is a smooth flat surface, among the reflected light components at the positions S1 to S3, only the reflected light at the position S3 where the angle (incident angle) with respect to the light source and the angle (reflection angle) with respect to the eyes are equal to each other enters the eyes of the observer. In the eyes of the observer, light is displayed only at the position S3 on the surface of the object and is not displayed at the other positions S1 and S2. That is, in a case in which the projection surface of the compression plate 40 is a smooth flat surface, a display image is not displayed on the projection surface even though the projection image PP is projected onto the projection surface by the projector 39.

On the other hand, as illustrated in FIG. 19, in a case in which the surface of the object is an uneven surface and the angles of the reflecting surfaces at the positions S4 to S6 are different, the angle (incident angle) with respect to the light source and the angle (reflection angle) with respect to the eyes can be equal to each other at each of the positions S4 to S6. In this case, since the reflected light from the positions S4 to S6 enters the eyes of the observer, light is displayed at each of the positions S4 to S6 on the surface of the object in the eyes of the observer. That is, in a case in which the projection surface of the compression plate 40 is an uneven surface and the projection image PP is projected onto the projection surface by the projector 39, the display image is displayed on the projection surface.

Therefore, it is preferable to perform a roughening process on the projection surface of the compression plate 40 in this embodiment such that the observer can visually recognize the display image in a case in which the projection image PP is projected by the projector 39. The roughening process is a process that forms unevenness on the surface of the projection surface. Examples of the roughening process include a surface texturing process and a satin finishing process. A roughening method is not particularly limited, and various known methods, such as a mechanical roughening process, an electrochemical roughening process, and a chemical roughening process, may be used.

Specifically, at least a partial region of at least one surface of the compression plate 40 which does not come into contact with the breast and onto which the projection image PP can be projected by the projector 39 is roughened. For example, in a case in which the skin line image is projected so as to be superimposed on the breast, at least a partial region of the surface (the upper surface 43A of the bottom portion 43 in FIG. 20) which is opposite to the contact surface 43B with the breast is roughened as illustrated in a schematic diagram of FIG. 20. In addition, even in a case in which the contact surface 43B of the bottom portion 43 with the breast is roughened, the display image is displayed on the bottom portion 43. However, it is desirable that the contact surface 43B with the breast is not roughened in order to suppress discomfort caused by the contact of the unevenness with the skin of the subject.

Figure 21:
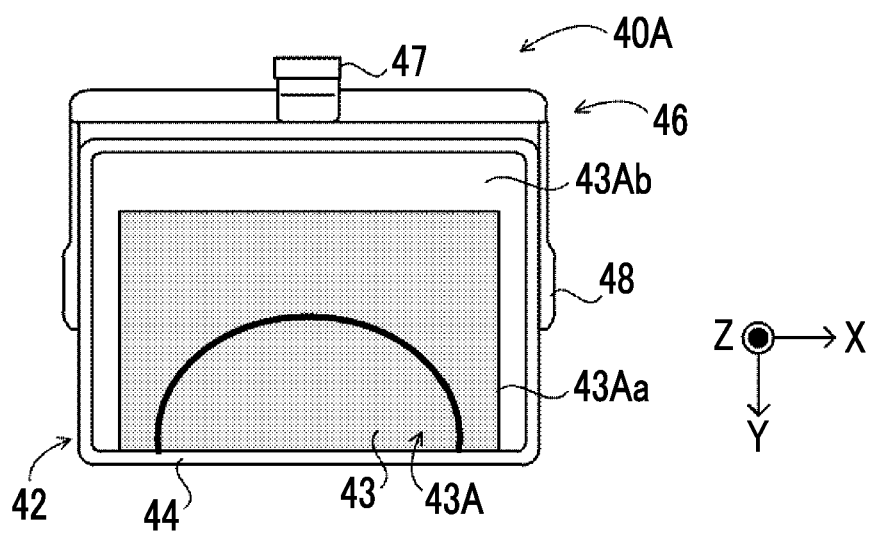
FIG. 21 is a diagram schematically illustrating an example of a compression plate in which a partial region of a projection surface is roughened.
Figure 22:
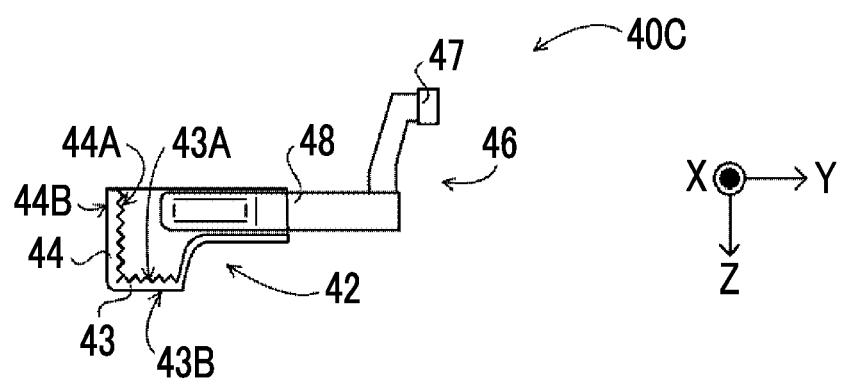
FIG. 22 is a diagram schematically illustrating an example of a compression plate having a roughened projection surface.

Further, assuming that the skin line image is projected so as to be superimposed on the breast, a skin line image projection region is limited to a region on the chest wall side in the upper surface 43A of the compression plate 40. Therefore, for example, as illustrated in FIG. 21, on the surface (the upper surface 43A in FIG. 21) opposite to the contact surface 43B with the breast, a region 43Aa on the chest wall side (the lower side in the Y direction in FIG. 21) may be roughened, and a region 43Ab on the side (the upper side in the Y direction in FIG. 21) opposite to the chest wall may not be roughened. For the same reason, particularly, in the compression plate 40 used for CC imaging, a partial region including the center of the breast in the left-right direction (the X direction in FIG. 21) may be roughened, and the end parts of the breast in the left-right direction (the X direction in FIG. 21) may not be roughened.

Further, for example, in a case in which the projection image PP can be projected onto plural surfaces, at least a partial region of each of the plurality of surfaces that do not come into contact with the breast may be roughened. For example, in a case in which the skin line image is projected onto the bottom portion 43 of the compression plate 40 and character information is projected onto the wall portion 44 (see FIG. 15), a surface (inner surface 44A) that intersects the surface (upper surface 43A) opposite to the contact surface 43B with the breast may be roughened in addition to the upper surface 43A as illustrated in a schematic diagram of FIG. 22. In addition, even in a case in which an outer surface 44B of the wall portion 44 is roughened, the display image is displayed on the wall portion 44. However, it is desirable that the outer surface 44B coming into contact with the chest wall is not roughened in order to suppress discomfort caused by the contact of the unevenness with the skin of the subject.

Further, for example, in a case in which both the bottom portion 43 and the wall portion 44 are small and it is difficult to project the projection image PP onto any surface as in the compression plate 40 for spot imaging, the projection image PP may be projected onto the support portion 46 that supports the compression plate 40. In this case, at least a partial region of at least one surface of the support portion 46 may be roughened.

In addition, in a case in which the region onto which the projection image PP can be projected is limited in each surface onto which the projection image PP is projected, only that region may be roughened.

It is preferable that the degree of roughening is equal to or smaller than the pixel size of the radiation detector 28 such that unevenness is not reflected in the radiographic image. In addition, as the roughness becomes smaller, the reflected light is more likely to diffuse. Therefore, it is possible to increase the visibility of the display image on the projection surface. On the other hand, in a case in which the roughness is too small, the breast is not seen through the compression plate. Therefore, it is preferable that the roughening is performed to the extent that the positioning of the breast is not hindered.

Specifically, in a case in which the projection surface of the compression plate 40 and the support portion 46 are configured to include the above-mentioned transparent resin, it is desirable that the arithmetic average roughness (Ra) of each roughened region is equal to or greater than 5 µm and equal to or less than 20 µm. In a case in which the arithmetic average roughness is equal to or less than 20 µm, it is possible to suppress the unevenness from being reflected in the radiographic image and to make it easy to see the display image on the projection surface. In a case in which the arithmetic average roughness is equal to or greater than 5 µm, it is suitable for checking the positioning of the breast through the compression plate 40. In other words, in a case in which the arithmetic average roughness is greater than 20 µm, the unevenness may be reflected in the radiographic image, which makes it difficult to see the display image on the projection surface. In a case in which the arithmetic average roughness is less than 5 µm, it may be difficult to see the breast through the compression plate 40.

As described above, the compression plate 40 according to this embodiment is a compression member that compresses the breast placed between the radiation source and the radiation detector. In the compression plate 40, at least a partial region of at least one surface that does not come into contact with the breast is roughened. Therefore, while the breast can be visually recognized through the compression plate 40, the display image can be displayed in a case in which the projection image PP is projected.

In addition, the use of the compression plate 40 and the support portion 46 whose projection surfaces are roughened such that light can be projected are not limited only to the mammography apparatus 10 according to the first and second embodiments of the present disclosure. The compression plate 40 and the support portion 46 can be used in any mammography apparatus including a radiation source, a radiation detector, a compression member which compresses the breast placed between the radiation source and the radiation detector and in which at least a partial region of at least one surface that does not come into contact with the breast is roughened, and an image projection unit that projects an image onto the roughened region of the compression member.

Further, as the compression plate 40 and the support portion 46 that can project light used in each of the above-described embodiments, the following configurations may be used in addition to the components subjected to the above-mentioned roughening process. For example, a transparent screen (see, for example, JP6606604B) that diffuses and/or reflects light projected by the projector 39 such that a display image can be visibly recognized and transmits light from the front and back surfaces may be attached to the projection surfaces of the compression plate 40 and the support portion 46. In this case, the transparent screen may be attached to the surfaces that come into contact with the skin of the subject, such as the contact surface 43B of the bottom portion 43 and the outer surface 44B of the wall portion 44. That is, the entire surfaces of the compression plate 40 and the support portion 46 can be used as the projection surfaces.

Further, in each of the above-described embodiments, the example in which the identification information is provided in the compression plate 40, the mammography apparatus 10 reads the identification information, and the first acquisition unit 60 acquires the projection surface size information with reference to the identification information and the compression plate information 53 has been described. However, the present disclosure is not limited thereto. For example, the shape of the attached compression plate 40, such as the size of the bottom portion 43 and the height of the wall portion 44, may be measured to directly acquire the projection surface size information of the compression plate 40. For example, a device that measures the distance to an object to be imaged, such as a time-of-flight (TOF) camera, can be used as a unit for measuring the shape of the compression plate 40. Specifically, the TOF camera is a camera that captures a distance image using a TOF method, irradiates an object to be imaged with light, such as infrared rays, and measures the distance between the TOF camera and the object to be imaged on the basis of the time until reflected light is received or a phase change between the emitted light and the received light. In the distance image captured by the TOF camera, each pixel has distance information indicating the distance between the TOF camera and the object to be imaged. In a case in which the shape of the compression plate 40 as an object to be imaged changes, the distance information of each pixel also changes. Therefore, the type of the compression plate can be identified by capturing the image of the compression plate 40 with the TOF camera.

Further, in each of the above-described embodiments, in a case in which it is determined that the size of the projection surface of the compression plate 40 indicated by the acquired projection surface size information is less than a predetermined size, the first acquisition unit 60 may stop the process of generating and projecting the subsequent projection image PP. The reason is that, for example, in a case in which the attached compression plate 40 is a small compression plate for spot imaging, it is difficult to project the projection image PP.

Further, in each of the above-described embodiments, the aspect in which the projection surface onto which the projection image PP is projected by the projector 39 is at least one surface of the compression plate 40 has been described. However, the present disclosure is not limited thereto. For example, the projector 39 may project the projection image PP onto the imaging table 30 of the mammography apparatus 10.

In addition, in each of the above-described embodiments, on the basis of the radiographic image of one of the right breast and the left breast, the generation unit 64 may generate the projection image PP including guide information related to the other breast. For example, in a case in which the radiographic image of the left breast is captured after the radiographic image of the right breast is captured, the projection image PP including guide information related to the left breast may be generated on the basis of an image obtained by reversing the radiographic image of the right breast in the left-right direction.

Further, in each of the above-described embodiments, the aspect in which the console 12 is an example of the information processing device according to the present disclosure has been described. However, devices other than the console 12 may have the functions of the information processing device according to the present disclosure. In other words, for example, the mammography apparatus 10 or an external device other than the console 12 may have some or all of the functions of the first acquisition unit 60, the second acquisition unit 62, the generation unit 64, and the projection control unit 66.

In addition, in each of the above-described embodiments, the aspect in which the radiographic image and the compression plate information 53 are stored in the storage unit 52 of the console 12 has been described. However, the place in which the radiographic image and the compression plate information 53 are stored is not limited to the storage unit 52. For example, the radiographic image and the compression plate information 53 may be stored in the storage unit 22 of the mammography apparatus 10 or may be stored in a device outside the radiography system 1.

Further, in each of the above-described embodiments, for example, the following various processors can be used as the hardware structure of processing units performing various processes such as the first acquisition unit 60, the second acquisition unit 62, the generation unit 64, and the projection control unit 66. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of plural FPGAs or a combination of a CPU and an FPGA). Further, plural processing units may be configured by one processor.

A first example of the configuration in which plural processing units are configured by one processor is an aspect in which one processor is configured by a combination of one or more CPUs and software and functions as plural processing units. A representative example of this aspect is a client computer or a server computer. A second example of the configuration is an aspect in which a processor that implements the functions of the entire system including plural processing units using one integrated circuit (IC) chip is used. A representative example of this aspect is a system-on-chip (SoC). In this way, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the information processing program 51 is stored (installed) in the storage unit 52 in advance has been described. However, the present disclosure is not limited thereto. The information processing program 51 may be recorded on a recording medium, such as a compact disc read only memory (CD-ROM), a digital versatile disc read only memory (DVD-ROM), or a universal serial bus (USB) memory, and then provided. In addition, the information processing program 51 may be downloaded from an external device through a network.

In the technology of the present disclosure, the above-described embodiments may be appropriately combined with each other. The contents described and illustrated above are detailed descriptions of portions related to the technology of the present disclosure and are merely examples of the technology of the present disclosure. For example, the description of the configurations, functions, operations, and effects is the description of examples of the configurations, functions, operations, and effects of portions related to the technology of the present disclosure. Therefore, unnecessary portions may be deleted or new elements may be added or replaced in the contents described and illustrated above, without departing from the scope and spirit of the technology of the present disclosure.

All of the documents, the patent applications, and the technical standards described in the specification are incorporated by reference herein to the same extent as each individual document, each patent application, and each technical standard are specifically and individually stated to be incorporated by reference.

What is claimed is:

1. An information processing device comprising at least one processor, wherein the processor is configured to:
    acquire a radiographic image captured by irradiating a breast compressed by a compression member with radiation;
    generate a projection image, which includes guide information serving as a guide in a case in which the breast is compressed and is capable of identifying whether the guide information is related to a right breast or a left breast, on the basis of a shape of the breast in the compressed state indicated by the radiographic image; and
    control an image projection unit which projects the projection image onto a first projection surface of the compression member such that the projection image is projected onto the first projection surface.

2. The information processing device according to claim 1, wherein the processor is configured to:
    generate the projection image while changing a display aspect depending on whether the guide information is related to the right breast or the left breast; and
    control the image projection unit such that the projection image is projected onto the first projection surface.

3. The information processing device according to claim 1, wherein the processor is configured to:
    generate the projection image including the guide information and left-right information indicating whether the guide information is related to the right breast or the left breast; and
    control the image projection unit such that the projection image is projected onto the first projection surface.

4. The information processing device according to claim 1, wherein:
    the image projection unit projects an image onto a second projection surface different from the first projection surface of the compression member in addition to the first projection surface, and
    the processor is configured to:
    generate the projection image including the guide information and left-right information indicating whether the guide information is related to the right breast or the left breast; and
    control the image projection unit such that the guide information is projected onto the first projection surface and the left-right information is projected onto the second projection surface.

5. An information processing method comprising:
    acquiring a radiographic image captured by irradiating a breast compressed by a compression member with radiation;
    generating a projection image, which includes guide information serving as a guide in a case in which the breast is compressed and is capable of identifying whether the guide information is related to a right breast or a left breast, on the basis of a shape of the breast in the compressed state indicated by the radiographic image; and
    controlling an image projection unit which projects the projection image onto a first projection surface of the compression member such that the projection image is projected onto the first projection surface.

6. A non-transitory computer-readable storage medium storing an information processing program that causes a computer to perform a process comprising:
    acquiring a radiographic image captured by irradiating a breast compressed by a compression member with radiation;
    generating a projection image, which includes guide information serving as a guide in a case in which the breast is compressed and is capable of identifying whether the guide information is related to a right breast or a left breast, on the basis of a shape of the breast in the compressed state indicated by the radiographic image; and
    controlling an image projection unit which projects the projection image onto a first projection surface of the compression member such that the projection image is projected onto the first projection surface.

* * * * *